United States Patent
Holcomb

(10) Patent No.: US 10,598,620 B2
(45) Date of Patent: Mar. 24, 2020

(54) NONDESTRUCTIVE TESTER

(71) Applicant: Grid Logic Incorporated, Lapeer, MI (US)

(72) Inventor: Matthew J. Holcomb, Metamora, MI (US)

(73) Assignee: Grid Logic Incorporated, Lapeer, MI (US)

( * ) Notice: Subject to any disclaimer, the term of this patent is extended or adjusted under 35 U.S.C. 154(b) by 103 days.

(21) Appl. No.: 15/167,257

(22) Filed: May 27, 2016

(65) Prior Publication Data

US 2016/0356735 A1    Dec. 8, 2016

Related U.S. Application Data

(60) Provisional application No. 62/272,580, filed on Dec. 29, 2015, provisional application No. 62/170,978, filed on Jun. 4, 2015.

(51) Int. Cl.
| | | |
|---|---|---|
| *G01N 27/02* | (2006.01) | |
| *G01N 27/82* | (2006.01) | |
| *B22F 3/105* | (2006.01) | |

(52) U.S. Cl.
CPC .......... *G01N 27/025* (2013.01); *G01N 27/82* (2013.01); *B22F 3/1055* (2013.01); *B22F 2202/07* (2013.01); *Y02P 10/295* (2015.11)

(58) Field of Classification Search
CPC .......... G01N 27/025; G01N 27/82; B22F 3/00
See application file for complete search history.

(56) References Cited

U.S. PATENT DOCUMENTS

| | | | | | |
|---|---|---|---|---|---|
| 4,785,243 | A | * | 11/1988 | Abramczyk | G01N 27/9013 324/232 |
| 5,446,379 | A | * | 8/1995 | Machi | G01N 27/82 324/207.17 |
| 6,150,809 | A | * | 11/2000 | Tiernan | G01N 27/82 324/225 |
| 9,261,573 | B1 | * | 2/2016 | Radparvar | G01R 33/323 |
| 2004/0222789 | A1 | * | 11/2004 | Pinsky | G01N 27/72 324/261 |
| 2005/0253594 | A1 | * | 11/2005 | Eberhardt | G01R 27/2652 324/637 |
| 2007/0085534 | A1 | * | 4/2007 | Seki | G01R 33/02 324/248 |
| 2009/0295407 | A1 | * | 12/2009 | Blew | G01R 27/2652 324/637 |
| 2014/0228671 | A1 | * | 8/2014 | Subramaniam | A61B 5/05 600/409 |
| 2015/0008928 | A1 | * | 1/2015 | Miles | G01V 3/28 324/339 |

* cited by examiner

*Primary Examiner* — Akm Zakaria
(74) *Attorney, Agent, or Firm* — Stephen M. De Klerk

(57) ABSTRACT

The invention provides a nondestructive tester that includes a coil for positioning adjacent a surface of an object, a voltage source connected to the coil to apply a forward power to the coil, a measurement circuit connected to the coil to measure a reflected power from the coil due to the forward power, and an analyzer connected to the measurement circuit and determining a result of a function of the reflected power to the forward power and utilizing a result of the function to determine whether a feature presence at or below the surface.

12 Claims, 7 Drawing Sheets

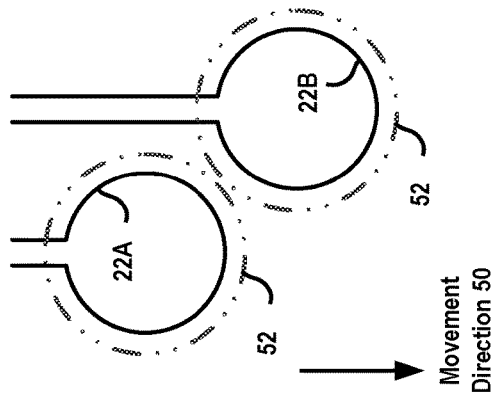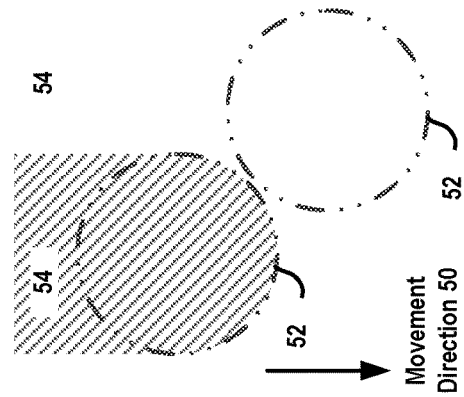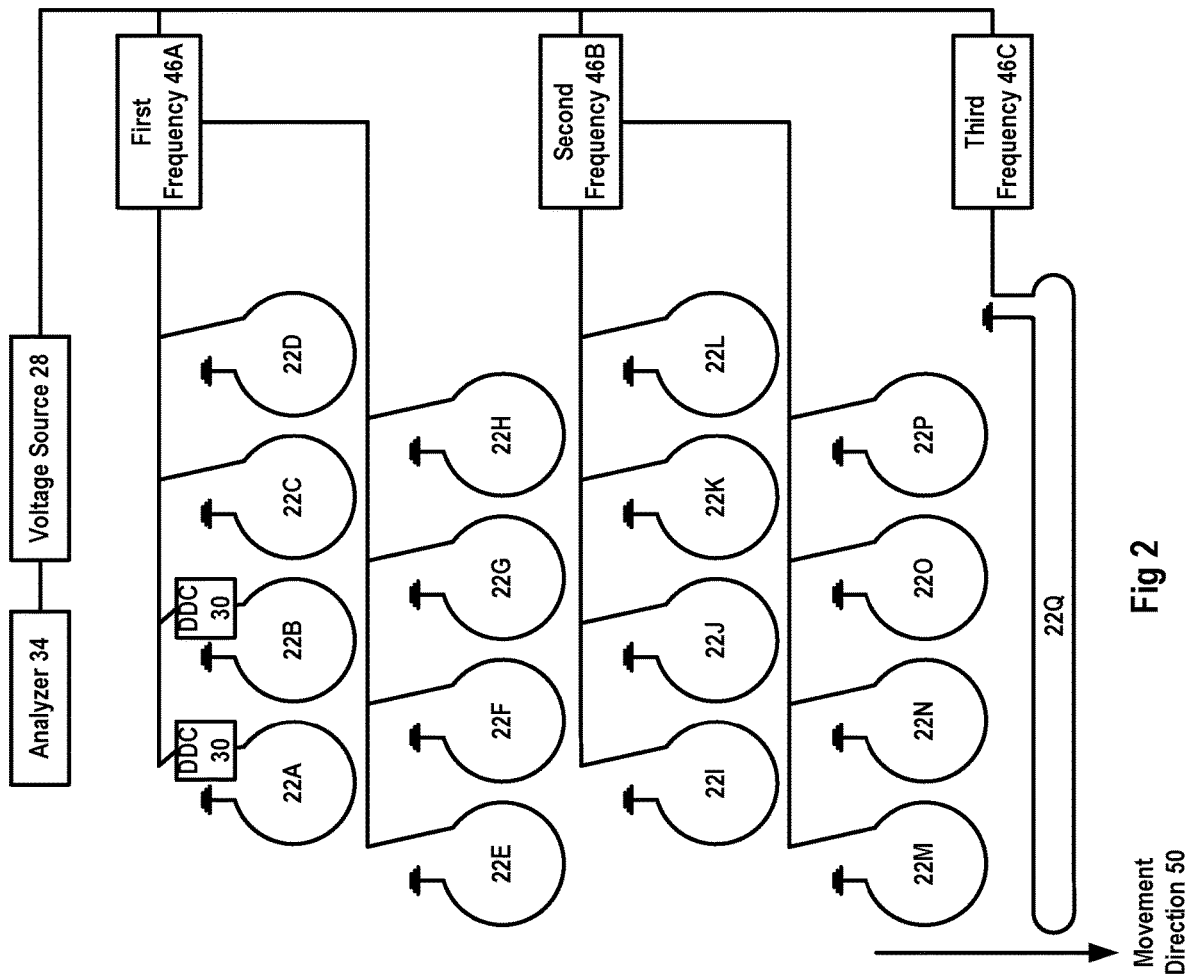

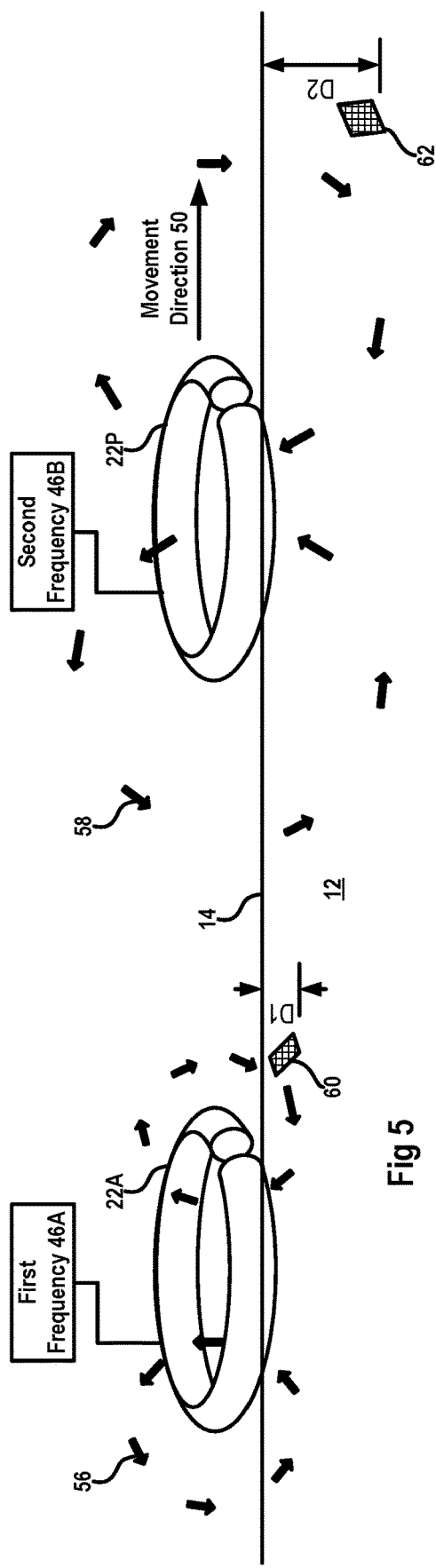
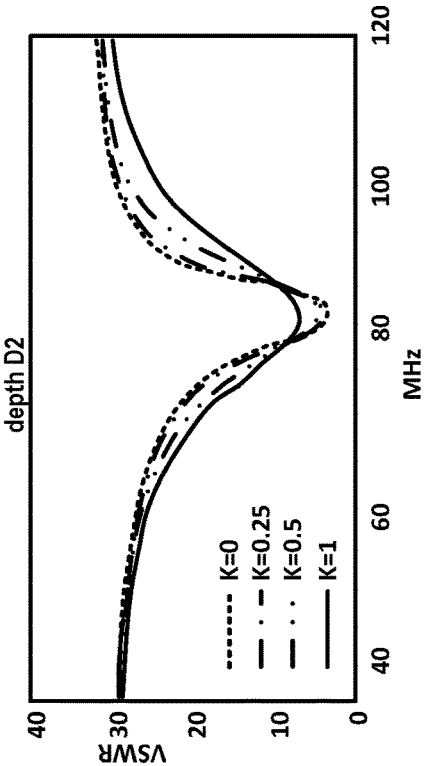
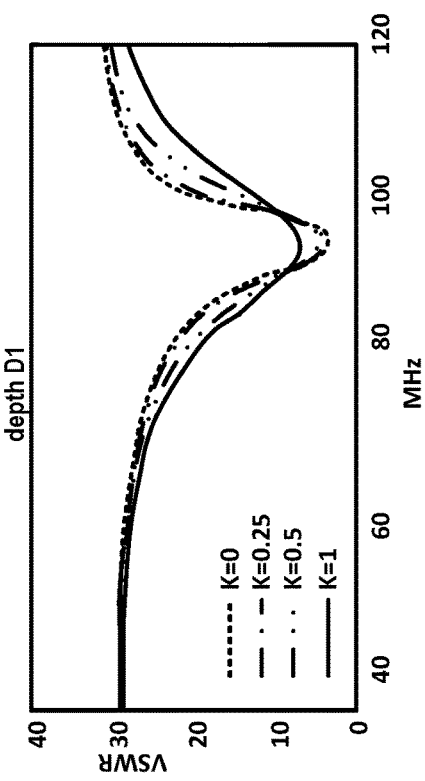

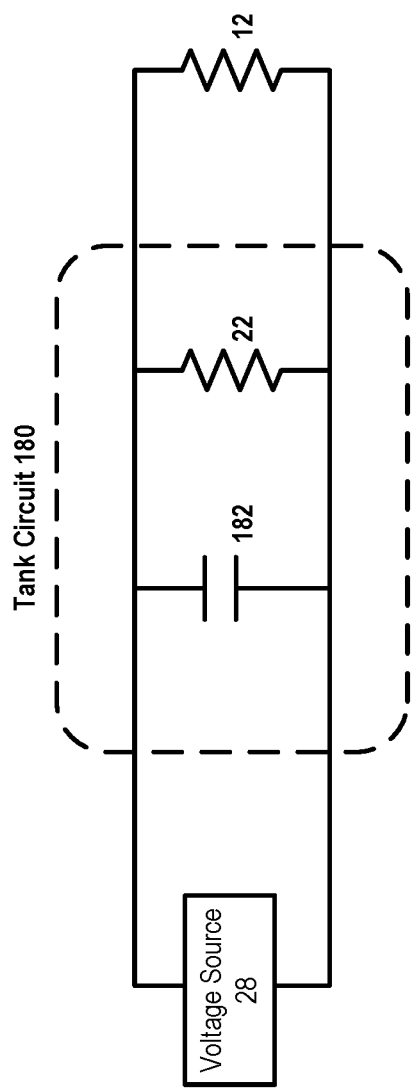

NONDESTRUCTIVE TESTER

CROSS-REFERENCE TO RELATED APPLICATIONS

This application claims priority from U.S. Provisional Patent Application No. 62/170,978, filed on Jun. 4, 2015 and U.S. Provisional Patent Application No. 62/272,580, filed on Dec. 29, 2015, each of which is incorporated herein by reference in their entirety.

BACKGROUND OF THE INVENTION

1). Field of the Invention

This invention relates to a nondestructive tester and to nondestructive detection method.

2). Discussion of Related Art

Traditional casting and machining techniques usually involve a selection of an alloy that is cast into predetermined shape and subsequently machined to obtain a desired shape. Relatively sophisticated shapes can be obtained using computer numerically controlled (CNC) machining techniques.

Three-dimensional (3D) printing techniques have become more common for manufacturing of metal parts. For example, powder or other granular material may be loosely deposited onto a two-dimensional surface and then be coagulated or melted so that they form a two-dimensional (2D) shape after solidification. Each 2D shape has a small thickness and the thicknesses of subsequent 2D shapes that are formed on one another ultimately render a 3D shape.

3D printing has numerous advantages over traditional machining techniques because it allows for manufacturing of more advanced shapes (for example, shapes that have cavities inside), more advance materials engineering (for example, using powder particles that are composites), and thermal characteristics can be controlled during coagulation to obtain desired results (for example, higher strength).

3D printing is a desirable technique when high quality parts have to be manufactured. Such a high quality part is required to have few or no feature presences below its surface. Defects such as voids, inclusion of an element other than the alloy or element of the bulk part, areas that have received too much heat, or areas that have received too little heat are all examples of feature presences that may exist at or below a surface of a part. It is desirable to have a part tested during or after manufacture to detect feature presences that may be present at or below a surface of a part.

U.S. Pat. No. 9,194,687 assigned to Textron Innovations Inc. of Providence, R.I. describes a nondestructive system for measuring non-conductive coating thickness. A composite substrate is provided on a conductive layer is placed over a surface of the composite substrate. A plurality of non-conductive coating layers are deposited over the conductive layer. An eddy-current measuring coil formed on a printed circuit board is provided atop the coating layers. The coil has a driving trace with first and second driving electrodes, and a receiving trace having first and second receiving electrodes. A load administered to the first and second driving electrodes using an eddyscope is measured across the first and second driving electrodes to determine impedance. The measured impedance is used to determine a total thickness of the coating layers and whether an overall coating thickness is uniform.

U.S. Pat. No. 9,103,801 assigned to Mitsubishi Hitachi Power Systems Limited of Kanagawa, Japan describes a feature presence detection device for a turbine rotor blade. An eddy current probe is moveably inserted into a recess, and a rod provided with a signal line for transmitting a signal detected by an eddy current probe is moveable through a hole in a turbine casing and an air gap formed in the stationary blade diaphragm. A data analyzer determines a condition of a feature presence in the turbine rotor blade based on the signals detected by the eddy current probe.

U.S. Pat. No. 8,237,433 assigned to JENTEK Sensors Inc. of Waltham, Mass. describes methods for monitoring of stresses and other material properties. These methods use measurements of effective electrical properties, such as magnetic permeability and electrical conductivity, to infer the state of the test material, such as the stress, temperature, or overload condition. The sensors, which can be single element sensors or sensor arrays, can be used to periodically inspect selected locations, mounted to the test material, or scanned over the test material to generate two-dimensional images of the material properties. Magnetic field or eddy current based inductive and giant magnetoresistive sensors may be used on magnetizable and/or conducting materials, while capacitive sensors can be used for dielectric materials. Methods are also described for the use of state-sensitive layers to determine the state of materials of interest. These methods allow the weight of articles, such as aircraft, to be determined.

SUMMARY OF THE INVENTION

The invention provides a nondestructive tester that includes a coil for positioning adjacent a surface of an object, a voltage source connected to the coil to apply a forward power to the coil, a measurement circuit connected to the coil to measure a reflected power from the coil due to the forward power, and an analyzer connected to the measurement circuit and determining a result of a function of the reflected power to the forward power and utilizing a result of the function to determine whether a feature presence at or below the surface.

The nondestructive tester may include that the function at least includes a division of the reflected power by the forward power to determine a voltage standing wave ratio (VSWR) that is analyzed to determine whether a feature presence at or below the surface.

The nondestructive tester may further include a translation system connected to the coil and being operable to move the coil in a translation direction relative to the surface, wherein the analyzer determines whether a feature presence below subsequent areas of the surface.

The nondestructive tester may further include a plurality of coils moving in parallel paths relative to the surface, wherein the analyzer determines whether a feature presence along the parallel paths.

The nondestructive tester may include that different frequencies are applied to two of the coils so that the coils determine whether a feature presence exists at different depths, respectively, at or below the surface.

The nondestructive tester may include that the coils detect feature presences along the same path.

The nondestructive tester may include that the coils are detailed inspection coils that may further include a general inspection coil spanning the paths and preceding the detailed inspection coils while traveling past the surface.

The nondestructive tester may include that the analyzer includes a display module that generates a two-dimensional map showing feature presences detected by the coils.

The nondestructive tester may further include a plurality of modules. Each module may include a plurality of coils, a master controller, an analog-to-digital module connected to the coils of the module to collect analog data from the coils and convert the analog data to digital data for each coil and a memory connected to the analog-to-digital module, the digital data being stored by the master controller in the memory.

The nondestructive tester may include that the analyzer collects the data from the memory of the modules.

The nondestructive tester may include that the coils of a module are located in a layout over a two-dimensional area and the layouts of the modules are identical.

The nondestructive tester may further include a frame, a retainer for the object mounted to the frame and a coil holder mounted to the frame, the coils being held by the coil holder.

The nondestructive tester may include that the coil holder is mounted for movement relative to the frame.

The invention also provides a nondestructive detection method including locating a coil adjacent a surface of an object, applying a forward power to the coil, measuring a reflected power from the coil due to the forward power, and determining a result of a function of the reflected voltage to the forward power and utilizing a result of the function to determine whether a feature presence at or below the surface.

BRIEF DESCRIPTION OF THE DRAWINGS

The invention is further described by way of example with reference to the accompanying drawings, wherein:

FIG. 2 is a plan view of coils connected to a voltage source and an analyzer of the nondestructive tester;

FIG. 3 is a plan view of two of the coils;

FIG. 4 is view similar to FIG. 3 showing overlapping paths of magnetic fields created by the coils;

FIG. 5 is a perspective view illustrating detection of feature presences at different depths at or below a surface of an object;

FIG. 6 is a graph of voltage standing wave ratio (VSWR) spectra of one of the coils in FIG. 4;

FIG. 7 is a graph of VSWR of another one of the coils in FIG. 4;

FIG. 12 shows a tank circuit that is connected to a voltage source.

DETAILED DESCRIPTION OF THE INVENTION

Figure 1:
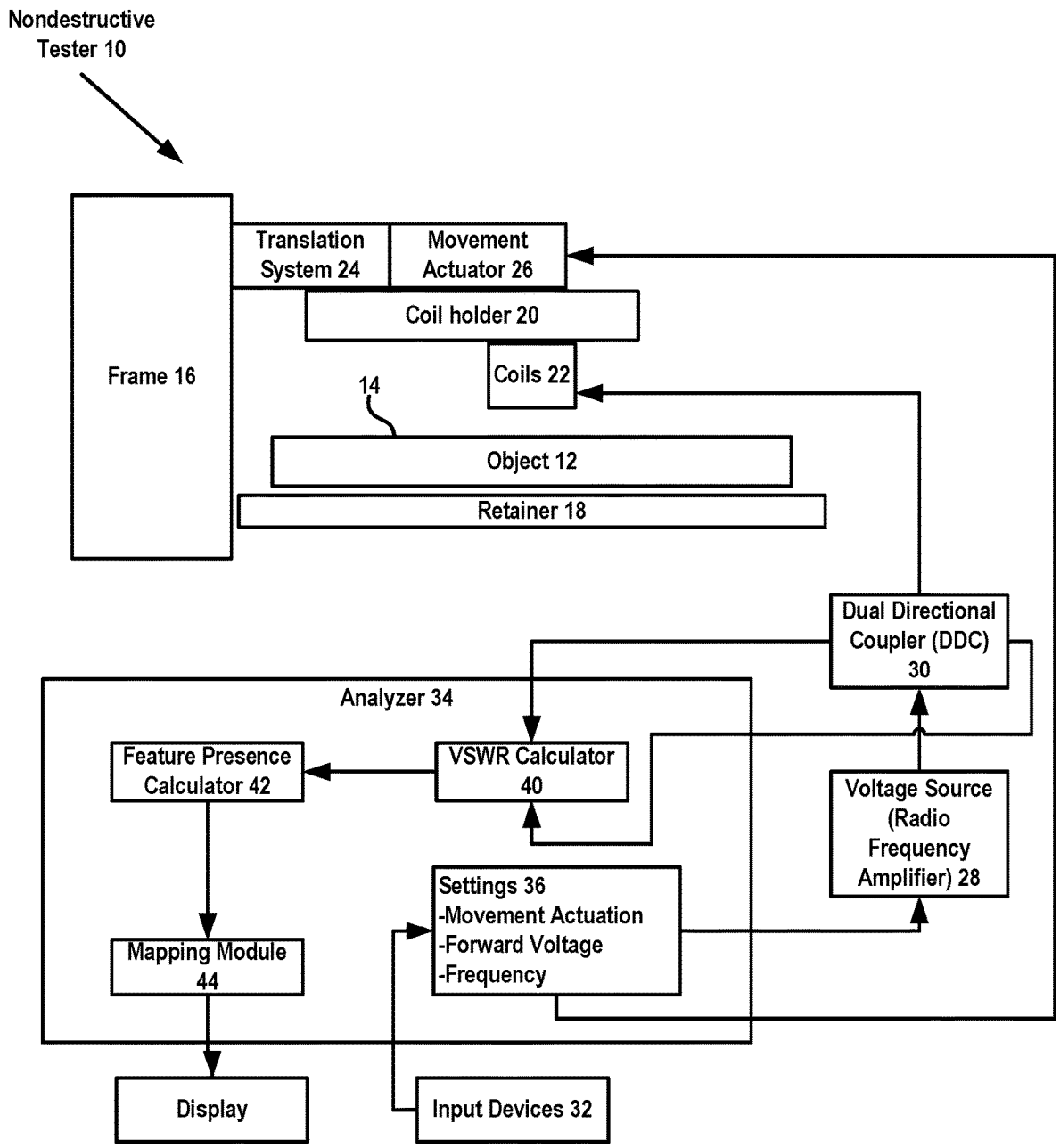
FIG. 1 is a block diagram of a nondestructive tester according to an embodiment of the invention.

FIG. 1 of the accompanying drawings illustrates a nondestructive tester 10 according to an embodiment of the invention, that is used for analyzing an object 12 to determine whether a feature presence exists at or below a surface 14 of the object. The nondestructive tester 10 includes a frame 16, a retainer 18, a coil holder 20, a plurality of coils 22, a translation system 24, a movement actuator 26, a voltage source 28 (typically a radio frequency amplifier), a dual directional coupler 30, input devices 32, a display 33 and an analyzer 34.

The retainer 18 is mounted to the frame 16. The coils 22 are located on and held by the coil holder 20. The coil holder 20 is mounted through the translation system 24 to the frame 16 so that the coils 22 are located adjacent to the surface 14 of the object 12. The translation system 24 allows for translation movement of the coil holder 20 together with the coils 22 relative to the frame 16. The movement actuator 26 is connected between the coil holder 20 and the translation system 24. Actuation of the movement actuator 26 causes movement of the coil holder 20 relative to the frame 16 on the translation system 24.

The analyzer 34 includes settings 36, a VSWR calculator 40, a feature presence calculator 42 and a mapping module 44.

The settings 36 include movement actuation, forward voltage and frequency. The settings 36 can be adjusted by the input and output devices 32. The movement actuator 26 receives an input from the settings 36 to cause movement of the coil holder 20 relative to the frame 16. The voltage source 28 receives a voltage and a frequency input from the settings 36. The voltage source 28 applies a voltage at a frequency as set in the settings 36 to the coils 22.

The dual directional coupler 30 measures a forward voltage to one of the coils 22 and a reflected voltage from the respective coils 22. The VSWR calculator 40 is connected to the dual directional coupler 30 and records the wave characteristics such as voltage amplitude and frequency of the forward voltage and the reflected voltage. The dual directional coupler 30 may for example measure power and then calculate voltage from the square root of the power. The VSWR calculator 40 calculates a VSWR by dividing the reflected voltage by the forward voltage according to the formula VSWR=(1+Gamma)/(1−Gamma) where Gamma is the absolute magnitude of the reflected voltage to the absolute value of the forward voltage as calculated according to the formula Gamma=(Reflected Power/Forward Power)^0.5. The dual directional coupler 30 thus forms part of a measurement circuit and the analyzer 34 is connected to the measurement circuit and determines a result of a function of the reflected power to the forward power. The function at least includes a division of the reflected power by the forward power to determine a voltage standing wave ratio (VSWR) that is analyzed to determine whether a feature presence at or below the surface The feature presence calculator 42 is connected to the VSWR calculator 40 for purposes of determining whether a feature presence is detected based on the VSWR calculated by the VSWR calculator 40 (The reflected voltage is thus indirectly analyzed to detect a feature presence at or below the surface 14). VSWR calculator 40 thus utilizes a result of the function to determine whether a feature presence at or below the surface. The feature presence may for example be a degree of consolidation of a powder, surface or subsurface defects, cracks or different microstructures of the material. The mapping module 44 is connected to the feature presence calculator 42 and the settings 36. The mapping module 44 uses the movement actuation within the settings 36 to show one or more feature presences as determined by the feature presence calculator 42 on a two-dimensional map. The mapping module 44 provides the map to the input and output devices 32. The input and output devices 32 may for example include a computer monitor that allows an operator to view the two-dimensional map that shows the location of the feature presences, whether they are at the surface 14, or their respective depths below the surface 14.

FIG. 2 shows that a plurality of coils 22A to Q are provided. The coils 22A to Q are all connected to the voltage source 28. The voltage source 28 provides a voltage at a first frequency 46A to the coils 22A to H and at a second frequency 46B to the coils 22I to P. The first frequency 46A is relatively low and the second frequency 46B is relatively high. The voltage source 28 provides the voltage at a third frequency 46C to the coil 22Q. The third frequency 46C is typically between the first frequency 46A and the second frequency 46B. A size of a feature determines the skin depth that should be targeted. The skin depth determines the frequency that should be used. The frequency determined the size of the coil that is required. The size of the coil is thus a function of the size of the feature that should be detected.

The coils 22A to P are single turn coils that have the same surface area. The coil 22Q is an elongate single turn coil that has the same surface area as any one of the coils 22A to P so that its inductance is also the same. The coil 22Q has a surface area that is preferably no more than 20% larger or smaller than any one of the coils 22A to P.

The coils 22A to Q travel in parallel paths as they move in a movement direction 50. The coil 22Q precedes the coils 22A to P and the path of the coil 22Q spans across the paths of the coils 22A to P. The coil 22Q is a general inspection coil that can be used to identify an area of general interest while the coils 22A to Q move relatively fast in the movement direction. After the area of general interest has been identified, the coils 22A to P serve as detailed inspection coils that can be used to further examine the area while the coils 22A to Q move more slowly in the movement direction 50.

FIG. 3 shows the coils 22A and 22F and magnetic fields 52 that are generated by the coils 22A and 22F. The magnetic fields 52 do not overlap or there is a minimal amount of overlap between them. FIG. 4 shows paths 54 that have been exposed to the magnetic fields 52 of FIG. 3. Although the magnetic fields 52 do not overlap, the paths 54 do overlap and ensure that no gap exists between regions inspected by the magnetic fields 52 of the coils 22A and 22F.

For non-magnetic metals, eddy currents flow within a certain distance from the surface of the material. The distance within the metal at which the eddy current is reduced to approximately 37% of the value at the surface is called the skin depth δ and can be written as, $$\delta = \sqrt{\frac{\rho}{\pi f \mu}} \quad [1]$$

where ρ is the resistivity and μ is the permeability of the material, and f is the frequency of the magnetic field.

For simple shaped (e.g. flat or cylindrical) materials placed in a uniform alternating magnetic field, the power absorbed by the part (PI) can be written as:

$$P_w = \frac{\rho}{\delta} A K H^2 = A K H^2 \sqrt{\pi f \mu \rho} \quad [2]$$

where ρ is the resistivity of the material, δ is the skin depth, A is the part surface exposed to the magnetic field, K is a power transfer factor that depends on part geometry relative to the applied magnetic field, and H is the magnetic field strength.

As shown in FIG. 5, the coil 22A, because it is exposed to the first frequency 46A, creates a magnetic field 56 of a relatively low magnitude. The magnetic field 56 couples with the object 12 up to a depth D1 which is the skin depth corresponding to the frequency of the magnetic field 56. The coil 22P is exposed to the second frequency 46B and generates a magnetic field 58 at a lower frequency than the magnetic field 56. The magnetic field 58 couples with the object 12 to depth D2 that is more than the depth D1. The coil 22A is more suitable for detecting a feature presence 60 within the depth D1, but is unsuitable for detecting a feature presence 62 that is at a depth that is more than D1 at or below the surface 14. The coil 22P is suitable for detecting the feature presence 62 and the feature presence 60. If both coils 22A and 22P detect a feature presence, it indicates that the feature presence is within the depth D1. If the coil 22A does not feature presence and the coil 22P detects a feature presence, the feature presence is at a depth more than D1 and less than D2.

FIGS. 6 and 7 illustrate VSWR for the coils 22A and 22P in FIG. 5, respectively. The coil 22A couples more effectively with the object 12 at a higher frequency of about 95 MHz and the first frequency 46A is selected to be approximately 95 MHz.

Recall that the VSWR of the coil 22A describes how the incident RF power is transmitted or reflected from the coil 22A. This quantity is independent of the incident power on the coil 22A. FIG. 6 shows calculated VSWRs for a tank circuit with a resonant frequency of approximately 95 MHz and increasing values of the coupling K. The overall shape of the VSWR changes as K increases. Changes in K reflect changes in the degree of coupling.

The coil 22P couples more effectively with the object 12 at a lower frequency of approximately 80 MHz and the second frequency 46B is selected to be approximately 80 MHz. A lower VSWR indicates better coupling and less reflections at a given frequency. A feature presence results in less coupling and a higher or lower VSWR at the given frequency. The feature presence is thus detected if the VSWR increases or decreases. A threshold of default detection may for example be set if VSWR increases or decreases by 50%, 75% or 100%.

A tank circuit has a resonant frequency that can be expressed as:

$$f = 1/2\pi\sqrt{LC} \quad [3]$$

where L is the inductance of the coil and C is the capacitance of the capacitors in the tank circuit, and f is the frequency of the magnetic field.

Power transfer is a strong function of electrical dimension (d/δ) of material

Power Transfer Factor increases with d>>δ

Specific Power (W/cm^3) decreases with d>>δ

Good Power Transfer: d/δ~6 (ideal sphere)

A larger effective particle size increases the resonant frequency of the coil 22A Variations in the particle size distribution Increased electrical dimension due to sintering and melting of the material Inductance of the powder decreases with consolidation Inductance of powder is in parallel to the coil 22A inductance.

Figure 8:
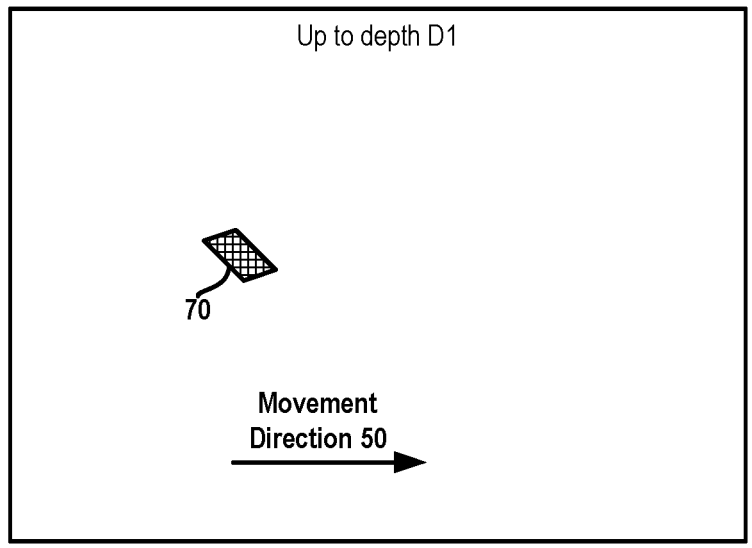
FIG. 8 is map that is generated on a monitor to show feature presences up to a first depth.
Figure 9:
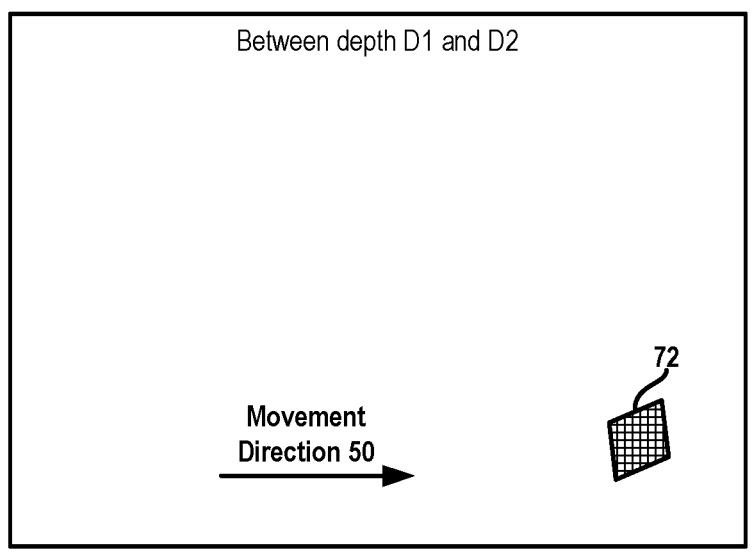
FIG. 9 is a map that is generated on a monitor to show feature presences between the first depth and second depth.

FIGS. 8 and 9 show maps that are generated for an operator to see the feature presences. FIG. 8 shows the feature presence 60 of FIG. 5 as an inclusion 70 on the map. FIG. 8 shows the feature presence 62 as an inclusion 72 on the map. The inclusions 72 and 70 are offset in the movement direction 50. In addition, because the coils 22A and 22P do not move on the same path, but instead move on parallel paths that are spaced from one another, the inclusions 70 and 72 are offset from one another in a direction orthogonal to the movement direction 50. Other ones of the coils, for example coils 22A and 22I, will detect feature presences at different depths along the same path.

Figure 10:
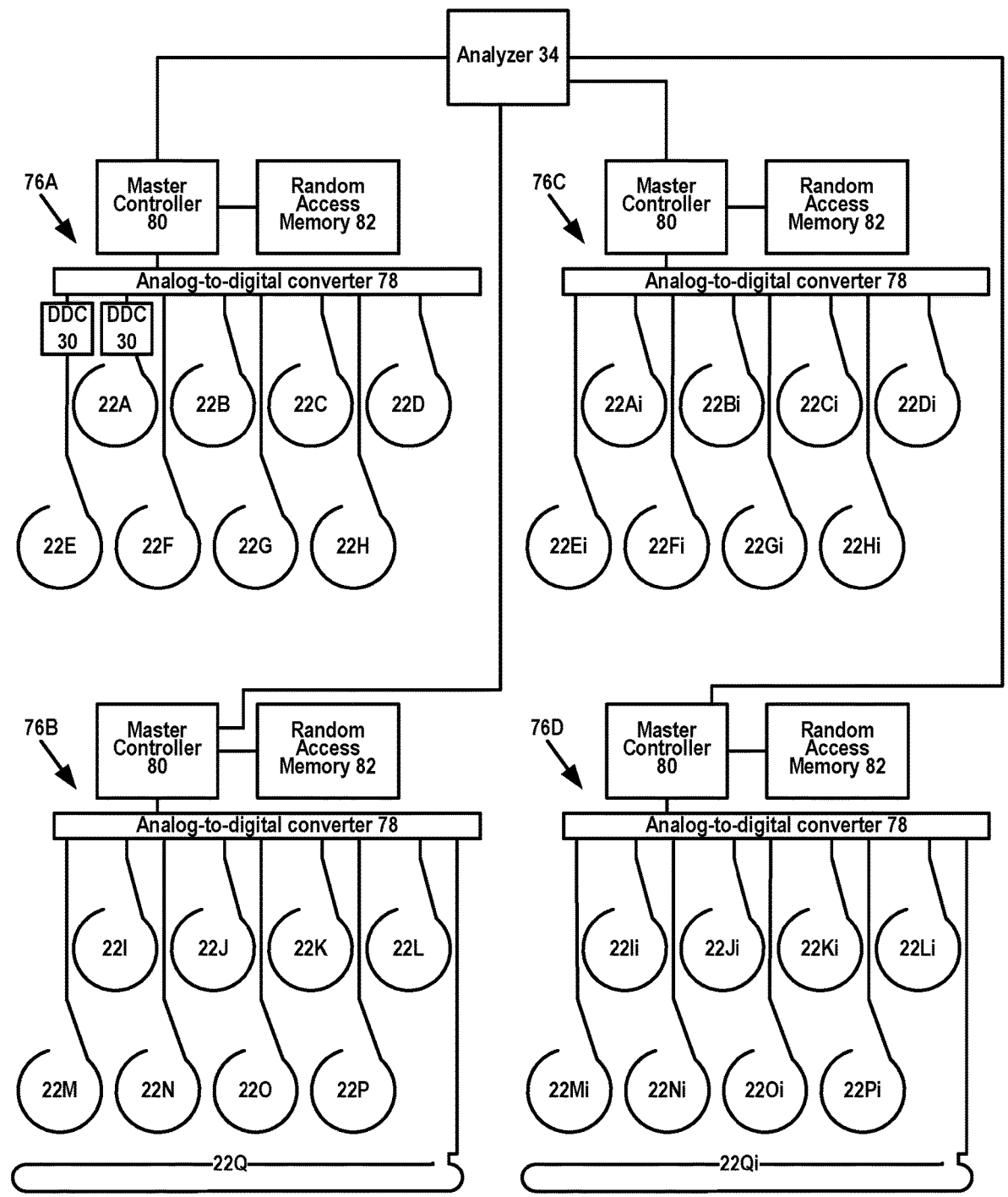
FIG. 10 is a plan view of a plurality of modules for distributed data collection.

As shown in FIG. 10, a plurality of modules 76A to D are provided. Each one of the modules 76A to D has a respective analog-to-digital converter 78, a respective master controller 80, and a respective random access memory 82. The module 76A further includes the coils 22A to H that are individually connected through respective dual directional couplers 30 to the analog-to-digital converter 78. The components shown in FIG. 10 provide a measurement circuit for measuring and recording forward and reflected voltages. In use, the respective dual directional coupler 30 measures a forward voltage to one of the coils 22A to H and measures a reflected voltage from the respective coils 22A to H. The analog-to-digital converter 78 converts the respective forward and reflected voltages to digital values representing the respective voltage wave as hereinbefore described. The analog-to-digital converter 78 is connected to the master controller 80. The master controller 80 is programmed to provide instructions to the analog-to-digital converter 78 for purposes of data collection and conversion to digital data. The master controller 80 is further connected to the random access memory 82. The master controller 80 downloads the digital data from the analog-to-digital converter 78 and stores the digital data in the random access memory 82. The digital data collected by the analog-to-digital converter 78 is stored in the random access memory 82 in real time. The master controller 80 then provides the digital data in the random access memory 82 to the analyzer 34. The transfer of digital data from the random access memory 82 to the analyzer 34 may be done in real time or at a later, for example after a scan of an object has been completed.

The module 76B includes the coils 22A to Q. The analog-to-digital converter 78 of the module 76B collects analog voltage data from the coils 22A to Q and converts the analog voltage data to digital data. The master controller 80 of the module 76B stores the data in the random access memory 82 of the module 76B. The master controller 80 of the module 76B is connected to the analyzer 34 and transfers the data from the random access memory 82 of the module 76B to the analyzer 34. The same analyzer 34 thus receives data from both modules 76A and 76B.

The modules 76C and 76D are similar to the modules 76A and 76B and similar reference numerals indicate similar components. The module 76C includes further coils 22Ai to Hi. The module 76D includes further coils 22Ii to Qi. The master controllers 80, random access memory 82, analog-to-digital converters 78 and connecting lines form part of the dual directional coupler 30 shown in FIG. 1. The dual directional coupler 30 includes analog-to-digital converters 78 that collect voltage data independently from all the coils. The distributed nature of the modules 76A to D permits a per-module collection of data. Per-module collection of data is useful because it results in relatively short connecting lines between the coils and the respective analog-to-digital converters 78. The relatively short connecting lines result in fewer losses and an effective use of circuit board real estate. Furthermore, a large amount of data can be collected using multiple master controllers 80 and multiple random access memories 82, which is more than can be accomplished with a single master controller and random access memory.

Defects can be nonintrusively detected at or below a surface of an object. Defects are detected at multiple depths of the objects when viewed in side view and can be detected across a two-dimensional area or surface of the object in plan view. A large amount of data can be collected using a modular arrangement for a measurement circuit.

Figure 11:
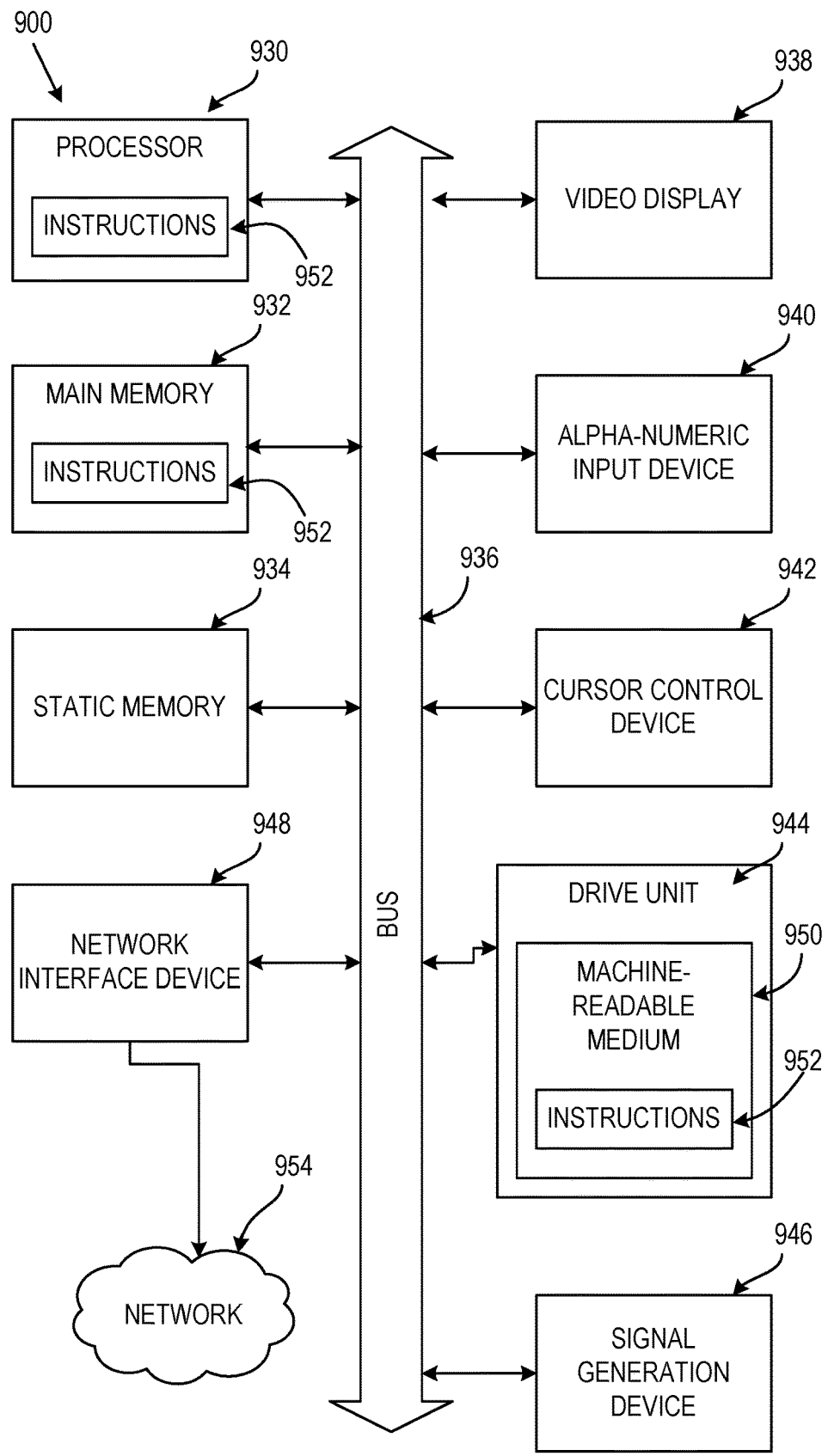
FIG. 11 is a block diagram of a machine in the form of an analyzer forming part of the nondestructive tester.

FIG. 11 shows a diagrammatic representation of a machine in the exemplary form of an analyzer 34 in the form of a computer system 900 within which a set of instructions, for causing the machine to perform any one or more of the methodologies discussed herein, may be executed. In alternative embodiments, the machine operates as a standalone device or may be connected (e.g., networked) to other machines. In a network deployment, the machine may operate in the capacity of a server or a client machine in a server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 900 includes a processor 930 (e.g., a central processing unit (CPU), a graphics processing unit (GPU), or both), a main memory 932 (e.g., read-only memory (ROM), flash memory, dynamic random access memory (DRAM) such as synchronous DRAM (SDRAM) or Rambus DRAM (RDRAM), etc.), and a static memory 934 (e.g., flash memory, static random access memory (SRAM, etc.), which communicate with each other via a bus 936.

The computer system 900 may further include a video display 938 (e.g., a liquid crystal displays (LCD) or a cathode ray tube (CRT)). The computer system 900 also includes an alpha-numeric input device 940 (e.g., a keyboard), a cursor control device 942 (e.g., a mouse), a disk drive unit 944, a signal generation device 946 (e.g., a speaker), and a network interface device 948.

The disk drive unit 944 includes a machine-readable medium 950 on which is stored one or more sets of instructions 952 (e.g., software) embodying any one or more of the methodologies or functions described herein. The software may also reside, completely or at least partially, within the main memory 932 and/or within the processor 930 during execution thereof by the computer system 900, the memory 932 and the processor 930 also constituting machine readable media. The software may further be transmitted or received over a network 954 via the network interface device 948.

FIG. 12 shows a tank circuit 180 that includes a capacitor 182 and one or more of the coils 22. The tank circuit 80 is connected to the voltage source 28.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A nondestructive tester comprising:
a general inspection coil;
a plurality of detailed inspection coils, each detailed inspection coil for positioning adjacent a surface of an object to create a magnetic field;
a translation system connected to the general inspection coil and the detailed inspection coils and being operable to move at least some of the detailed inspection coils in parallel paths in a translation direction relative to the surface, the general inspection coil spanning the paths and preceding the detailed inspection coils while traveling past the surface;
a tank circuit with at least one capacitor and having a resonant frequency f, wherein:

$$f=1/2\pi\sqrt{LC}$$

where L is the inductance of the respective detailed inspection coil and C is the capacitance of the at least one capacitor in the tank circuit, and f is the frequency of the magnetic field;
a voltage source connected to the tank circuit to apply a forward power to the detailed inspection coil;
a measurement circuit connected to the tank circuit to measure a reflected power from the tank circuit due to the forward power applied to the detailed inspection coil; and
an analyzer connected to the measurement circuit and determining a result of a function of the reflected power to the forward power and utilizing a result of the function to determine whether a feature is present at or below the surface along the parallel paths.

2. The nondestructive tester of claim 1, wherein the function at least includes a division of the reflected power by the forward power to determine a voltage standing wave ratio (VSWR) that is analyzed to determine whether a feature presence at or below the surface.

3. The nondestructive tester of claim 1, wherein different frequencies are applied to two of the detailed inspection coils so that the detailed inspection coils determine whether a feature presence exists at different depths, respectively, at or below the surface.

4. The nondestructive tester of claim 3, wherein at least some of the detailed inspection coils detect feature presences along a common path.

5. The nondestructive tester of claim 1, wherein the analyzer includes a display module that generates a two-dimensional map showing feature presences detected by the coils.

6. The nondestructive tester of claim 1, further comprising:
a plurality of modules, each module including:
a plurality of detailed inspection coils;
a master controller;
an analog-to-digital module connected to the detailed inspection coils of the module to collect analog data from the detailed inspection coils and convert the analog data to digital data for each detailed inspection coil; and
a memory connected to the analog-to-digital module, the digital data being stored by the master controller in the memory.

7. The nondestructive tester of claim 6, wherein the analyzer collects the data from the memory of the modules.

8. The nondestructive tester of claim 6, wherein the detailed inspection coils of a module are located in a layout over a two-dimensional area and the layouts of the modules are identical.

9. The nondestructive tester of claim 1, further comprising:
a frame;
a retainer for the object mounted to the frame; and
a coil holder mounted to the frame, the general inspection coil and the detailed inspection coils being held by the coil holder.

10. The nondestructive tester of claim 9, wherein the coil holder is mounted for movement relative to the frame.

11. The nondestructive tester of claim 1, wherein detailed inspection coil has a size that is selected to detect the feature.

12. A nondestructive detection method comprising:
locating a general inspection coil and a plurality of detailed inspection coils adjacent a surface of an object to create a respective magnetic field;
operating a translation system connected to the general inspection coil and the detailed inspection coils to move at least some of the detailed inspection coils in parallel paths in a translation direction relative to the surface, the general inspection coil spanning the paths and preceding the detailed inspection coils while traveling past the surface;
applying a forward power to the respective detailed inspection coil through a tank circuit with a resonant frequency f, wherein;

$$f=1/2\pi\sqrt{LC}$$

where L is the inductance of the detailed inspection coil and C is the capacitance of at least one capacitor in the tank circuit, and f is the frequency of the magnetic field;
measuring a reflected power from the tank circuit due to the forward power applied to the tank circuit; and
determining a result of a function of the reflected voltage to the forward power and utilizing a result of the function to determine whether a feature is present at or below the surface along the parallel paths.

* * * * *